United States Patent
Takeda et al.

(10) Patent No.: US 7,648,459 B2
(45) Date of Patent: Jan. 19, 2010

(54) ULTRASONIC PROBE

(75) Inventors: Junichi Takeda, Kawasaki (JP); Masashi Ozawa, Yokohama (JP)

(73) Assignee: Panasonic Corporation, Osaka (JP)

( * ) Notice: Subject to any disclaimer, the term of this patent is extended or adjusted under 35 U.S.C. 154(b) by 38 days.

(21) Appl. No.: 10/550,835

(22) PCT Filed: Mar. 24, 2004

(86) PCT No.: PCT/JP2004/004045

§ 371 (c)(1), (2), (4) Date: Sep. 23, 2005

(87) PCT Pub. No.: WO2004/084734

PCT Pub. Date: Oct. 7, 2004

(65) Prior Publication Data

US 2006/0241467 A1 Oct. 26, 2006

(30) Foreign Application Priority Data

Mar. 25, 2003 (JP) ............................. 2003-083489

(51) Int. Cl.
*A61B 8/00* (2006.01)
(52) U.S. Cl. ....................... 600/437; 600/446; 600/459; 310/334; 310/311
(58) Field of Classification Search ......... 600/437–459; 310/334–337, 311; 367/901
See application file for complete search history.

(56) References Cited

U.S. PATENT DOCUMENTS

| | | | | |
|---|---|---|---|---|
| 5,295,487 A * | 3/1994 | Saitoh et al. | ................ | 600/459 |
| 5,300,068 A * | 4/1994 | Rosar et al. | .................... | 606/34 |
| 5,810,009 A * | 9/1998 | Mine et al. | .................. | 600/459 |
| 6,100,626 A * | 8/2000 | Frey et al. | .................... | 310/334 |
| 7,063,666 B2 * | 6/2006 | Weng et al. | ................. | 600/439 |
| 2001/0031922 A1 * | 10/2001 | Weng et al. | ................. | 600/439 |
| 2002/0010414 A1 * | 1/2002 | Coston et al. | ................ | 604/20 |
| 2005/0096542 A1 * | 5/2005 | Weng et al. | ................. | 600/439 |
| 2006/0235300 A1 * | 10/2006 | Weng et al. | ................. | 600/439 |

FOREIGN PATENT DOCUMENTS

| | | |
|---|---|---|
| JP | 60-132544 | 7/1985 |
| JP | 1-291846 | 11/1989 |
| JP | 1989-172800 | 12/1989 |
| JP | 3-173546 | 7/1991 |
| JP | 5-220140 | 8/1993 |
| JP | 6-105844 | 4/1994 |
| JP | 9-139998 | 5/1997 |
| JP | 11-347032 | 12/1999 |

(Continued)

*Primary Examiner*—Long V Le
*Assistant Examiner*—Sanjay Cattungal
(74) *Attorney, Agent, or Firm*—Hamre, Schumann, Mueller & Larson, P.C.

(57) ABSTRACT

An ultrasonic probe according to the present invention includes: an ultrasonic element for transmitting and receiving an ultrasonic signal; a signal line for transmitting an electric signal to or from the ultrasonic element; and a ground line for supplying a ground potential to the ultrasonic element. The ultrasonic element is connected electrically with a sensor signal substrate and a sensor ground substrate. These substrates are connected electrically with the signal line and the ground line, respectively, via a cable substrate. The sensor ground substrate and the cable substrate are connected directly or via a relay ground substrate.

9 Claims, 5 Drawing Sheets

FOREIGN PATENT DOCUMENTS

| | | |
|---|---|---|
| JP | 2000-115891 | 4/2000 |
| JP | 2001-054194 | 2/2001 |
| JP | 2001-276078 | 10/2001 |
| JP | 2002-52024 | 2/2002 |
| JP | 2003-265470 | 9/2003 |

* cited by examiner

ULTRASONIC PROBE

TECHNICAL FIELD

The present invention relates to an ultrasonic probe for use in an ultrasonic diagnostic apparatus that emits ultrasonic waves to the inside of a body of a subject so as to create and display a tomographic image of the inside of the body based on the ultrasonic waves reflected at a boundary of each body tissue.

BACKGROUND ART

Ultrasonic diagnostic apparatuses transmit and receive ultrasonic waves to and from a living body so as to obtain two-dimensional information on the inside of the living body, and these apparatuses are utilized in various medical fields. Such ultrasonic diagnostic apparatuses are provided with a probe for transmitting ultrasonic waves to the inside of a body of a subject and receiving reflected waves from a body tissue. Such an ultrasonic diagnostic apparatus provided with a probe as a component thereof is disclosed in, for example, Japanese Patent No. 1746663 or the like.

FIG. 5 is a schematic cross-sectional view showing an example of a probe as a component of a conventional ultrasonic diagnostic apparatus. This ultrasonic probe includes a sensor portion 200, a cable portion 201, and a connector portion 202 to be connected to a main body of the ultrasonic diagnostic apparatus (not shown).

The sensor portion 200 includes an ultrasonic element 203 for transmitting and receiving ultrasonic waves, a sensor signal substrate 204 and a sensor ground substrate 205 connected electrically with the ultrasonic element 203, an acoustic matching plate 220 and an acoustic lens 207 provided on an ultrasonic wave transmitting/receiving surface of the ultrasonic element 203, and a backing layer 206 provided on a back surface (surface opposite to the ultrasonic wave transmitting/receiving surface) of the ultrasonic element 203. The sensor portion 200 further includes a sensor connector 217 connected with the sensor signal substrate 204 and the sensor ground substrate 205.

The cable portion 201 includes a plurality of signal wires 209, each including a signal line 209a and a ground line 209b, a cable substrate 208 connected with the signal wires 209, and a cable connector 218 connected with the cable substrate 208. In the cable portion 201, an outer periphery of the signal wires 209 is covered with a cable shield 210 and further is protected by a sheath 211. A shielding plate 219, which is a film formed of an insulating layer 219b and a conductive layer 219a formed on a surface of the insulating layer 219b, is arranged so as to surround the cable substrate 208 and the cable connector 218 as well as a part of an outer periphery of the sensor portion 200, and is connected with the cable shield 210.

The connector portion 202 includes a connector 215 for connecting with the main body and pins 216, each being connected with the signal line 209a or the ground line 209b. These components are accommodated in a connector housing 213. The connector housing 213 is provided with a conductive layer 214 on its inner wall surface. The cable shield 210 is connected with the conductive layer 214 and is to be connected with a frame ground or a signal ground of the main body of the ultrasonic diagnostic apparatus when the probe is connected with the main body of the ultrasonic diagnostic apparatus.

However, in the above conventional example, a ground electrode of the ultrasonic element 203 is connected with the ground line 209b through the sensor ground substrate 205, the sensor connector 217 as well as the cable connector 218, and the cable substrate 208. Accordingly, due to limitations on the number of connector poles and the like, it is difficult to secure a sufficient number of poles for a ground. When a sufficient number of poles are not secured for a ground, resistance between the sensor ground substrate and the cable substrate increases, and in the case where a noise current flows through the ground due to exposure to an electromagnetic environment, the ground potential varies, and image noise may be caused.

DISCLOSURE OF INVENTION

The present invention solves the above-mentioned conventional problem, and its object is to provide an ultrasonic probe that allows ground resistance in a connecting portion between a sensor portion and a cable portion to be reduced so as to cause less noise.

In order to achieve the above-mentioned object, an ultrasonic probe according to the present invention includes: an ultrasonic element for transmitting and receiving an ultrasonic signal; a signal line for transmitting an electric signal to or from the ultrasonic element; and a ground line for supplying a ground potential to the ultrasonic element.

The ultrasonic probe further includes: a sensor signal substrate and a sensor ground substrate connected electrically with the ultrasonic element; and a cable substrate for electrically connecting the sensor signal substrate and the sensor ground substrate with the signal line and the ground line, respectively, wherein the sensor ground substrate and the cable substrate are connected directly or via a relay ground substrate.

DESCRIPTION OF THE INVENTION

Figure 1:
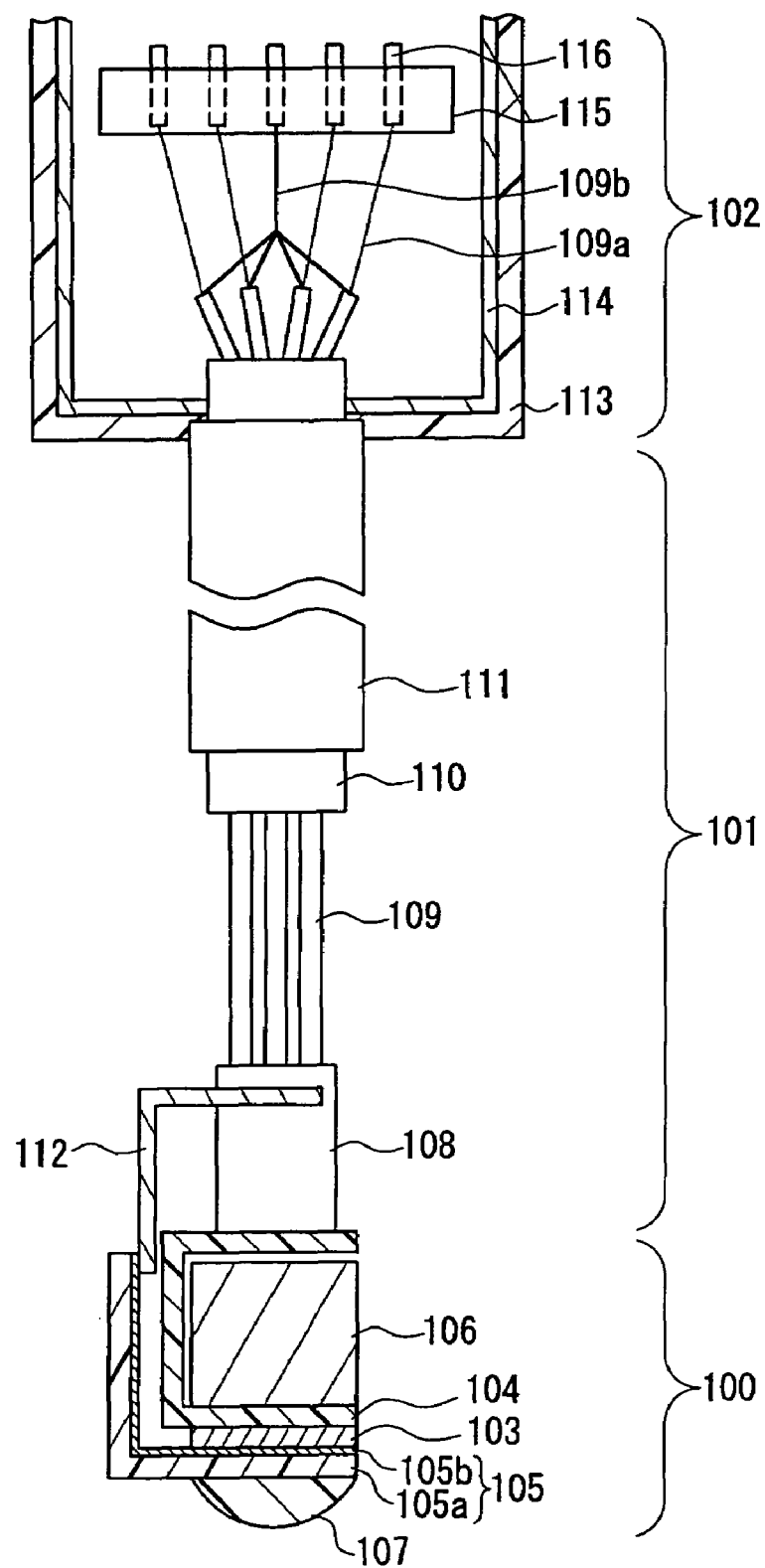
FIG. 1 is a cross-sectional view showing an example of an ultrasonic probe according to a first embodiment of the present invention.

In an ultrasonic probe according to the present invention, an ultrasonic element and a ground line are connected electrically, and accordingly a sensor ground substrate connected with the ultrasonic element and a cable substrate connected with the ground line are connected directly or via a relay ground substrate. Therefore, unlike the case where these substrates are connected via a connector, it is possible to avoid an increase in resistance due to limitations on the number of connector poles, resulting in a reduction in ground resistance between the sensor ground substrate and the cable substrate. Consequently, the reduction in ground resistance suppresses a change in ground potential due to a noise current induced by extraneous electromagnetic waves. As a result, an adverse effect on a reception signal due to the change in ground potential is reduced, and image noise can be prevented from being caused.

Preferably, in the above ultrasonic probe, at least a part of the sensor signal substrate is covered with the sensor ground substrate or the relay ground substrate.

Preferably, in the above ultrasonic probe, at least a part of the cable substrate is covered with the sensor ground substrate or the relay ground substrate.

Preferably, in the above ultrasonic probe, a connecting portion between the sensor signal substrate and the cable substrate is covered with the sensor ground substrate or the relay ground substrate.

According to the above-mentioned preferred examples, the sensor ground substrate or the relay ground substrate can function as a shield for shielding at least one of the sensor signal substrate, the cable substrate, and the connecting portion therebetween. Therefore, it is possible to suppress noise from being caused due to extraneous electromagnetic waves, and the ultrasonic probe exhibits increased durability to withstand electromagnetic waves.

Preferably, in the above ultrasonic probe, at least a part of the ultrasonic element is covered with the sensor ground substrate or the relay ground substrate. According to this preferred example, the ultrasonic probe exhibits increased durability to withstand electromagnetic waves.

Preferably, in the above ultrasonic probe, an ultrasonic wave transmitting/receiving surface, and further the ultrasonic wave transmitting/receiving surface and peripheral surfaces of the ultrasonic element are covered with the sensor ground substrate or the relay ground substrate. According to this preferred example, in addition to the effect of increasing durability of the ultrasonic probe to withstand electromagnetic waves, the sensor ground substrate or the relay ground substrate can function as an acoustic matching plate. In this case, there is no need to provide an acoustic matching plate additionally, resulting in an improvement in workability.

In the above preferred example, a plurality of grooves may be formed on a part of the sensor ground substrate or the relay ground substrate that covers the ultrasonic wave transmitting/receiving surface of the ultrasonic element, the grooves dividing the ultrasonic element electrically into a plurality of oscillators.

Hereinafter, embodiments of the present invention will be described with reference to the drawings.

First Embodiment

FIG. 1 is a view showing an example of an ultrasonic probe according to a first embodiment of the present invention. This ultrasonic probe includes a sensor portion 100 for converting an electric signal into an ultrasonic wave and transmitting the same to a living body as well as receiving a reflected wave from the living body and converting the same into an electric signal, a cable portion 101 for transmitting and receiving the electric signal to and from the sensor portion 100, and a connector portion 102 for connecting the probe with the a main body of an ultrasonic diagnostic apparatus.

The sensor portion 100 includes an ultrasonic element 103 and a sensor signal substrate 104 and a sensor ground substrate 105 connected electrically with the ultrasonic element 103. On an ultrasonic wave transmitting/receiving surface of the ultrasonic element 103, an acoustic matching plate may be provided so as to transmit and receive an ultrasonic wave efficiently. Further, on the ultrasonic wave transmitting/receiving surface of the ultrasonic element 103, an acoustic lens 107 is provided so as to converge the ultrasonic wave and increase the resolution in an area of interest in the living body. On a back surface (surface opposite to the ultrasonic wave transmitting/receiving surface) of the ultrasonic element 103, a backing layer 106 is provided so as to absorb the ultrasonic wave.

The ultrasonic element 103 is made of a material having piezoelectric properties, such as a piezoelectric ceramic of barium titanate or the like, for example. On a surface of the ultrasonic element 103, a signal electrode and a ground electrode made of a conductive material such as metal are formed, these electrodes being connected electrically with conductive portions of the sensor signal substrate 104 and the sensor ground substrate 105, respectively. The arrangement of these substrates is not particularly limited. For example, as shown in FIG. 1, the sensor signal substrate 104 may be arranged so as to cover the entire back surface of the ultrasonic wave element 103, and the sensor ground substrate 105 may be arranged so as to cover the entire ultrasonic wave transmitting/receiving surface of the ultrasonic element 103.

As the sensor signal substrate 104, an insulating substrate with a conductive layer formed on its surface is used. The insulating substrate is made of a polymeric material, such as, for example, epoxy resin, polyimide, polyethylene terephthalate, polysulphone, polycarbonate, polyester, polystyrene, polyphenylene sulfide, and the like. The conductive layer is made of metal, such as, for example, Ni, Cr, Au, Ag, Al, Cu, Ti, and the like. The thickness of the conductive layer is not particularly limited, and is 30 μm or less, for example. The conductive layer is patterned into a predetermined shape, and is connected electrically with the signal electrode of the ultrasonic element. This connection is made via solder and a conductive adhesive or the like or by mechanical contact, for example.

As the sensor ground substrate 105, an insulating substrate 105a with a conductive layer 105b formed on its surface can be used, as in the case of the sensor signal substrate. In particular, when the sensor ground substrate 105 is provided so as to cover the entire ultrasonic wave transmitting/receiving surface of the ultrasonic element 103, the thickness of the conductive layer is required to be set so as not to inhibit the transmission and reception of the ultrasonic wave. Such a thickness of the conductive layer is 30 μm or less, for example. Further, a substrate made of a conductive material such as metal also may be used as the sensor ground substrate 105.

Further, as shown in the example in FIG. 1, when the sensor ground substrate 105 is provided so as to cover the entire ultrasonic wave transmitting/receiving surface of the ultrasonic element 103, a material having an acoustic matching function may be used for the sensor ground substrate 105, which allows the sensor ground substrate 105 to function as an acoustic matching plate. In such a case, it is possible to reduce the materials to be laminated between the ultrasonic element and the acoustic lens, or to eliminate the need to provide an acoustic matching plate additionally. As a result, acoustic mismatching caused by an adhesive or the like between the sensor ground substrate and the acoustic matching plate can be suppressed, and the ultrasonic probe can be manufactured easily. The material having an acoustic matching function is made of, for example, a polymeric material such as, for example, epoxy resin, polyimide, polyethylene terephthalate, polysulphone, polycarbonate, polyester, polystyrene, polyphenylene sulfide, and the like and a metal material such as, for example, Ni, Cr, Au, Ag, Al, Cu, Ti, and the like that is formed on a piezoelectric plate with a thickness of 30 μm or less, for example. Alternatively, a material having conductive performance, such as a material made of a conductive plastic or graphite, is also useful.

The conductive layer 105b (in the case of a conductive substrate, the layer corresponds to this substrate) of the sensor ground 105 is connected electrically with the ground electrode of the ultrasonic element 103. This connection is made via solder and a conductive adhesive or the like or by mechanical contact, for example, as in the case of the conductive layer of the sensor signal substrate 104.

Preferably, as shown in FIG. 1, the sensor ground substrate 105 is arranged so as to cover at least a part of the sensor signal substrate 104. This arrangement allows the conductive layer 105b of the sensor ground substrate 105 to function as a shielding plate for shielding at least a part of the sensor signal substrate 104, thereby increasing durability to withstand electromagnetic waves. This arrangement can be realized by, for example, drawing the sensor signal substrate 104 and the sensor ground substrate 105 from the ultrasonic element 103 in the same direction (to the left side of the ultrasonic element in the example shown in FIG. 1).

In the example shown in FIG. 1, the ultrasonic element 103 and the conductive portion 105a of the sensor ground substrate 105 are connected directly. However, a conductive material such as, for example, a graphite plate may be provided between the ultrasonic element 103 and the conductive portion 105a. The sensor ground substrate 105 is provided over the entire ultrasonic wave transmitting/receiving surface of the ultrasonic element 103. However, the present invention is not limited thereto, and the sensor ground substrate 105 may be provided only over an end portion of the ultrasonic element 103. The ultrasonic element 103 and the sensor signal substrate 104 also may be connected directly or via a conductive material.

In the cable portion 101, a plurality of signal wires 109 are covered with a cable shield 110 and further are protected by a sheath 111. The cable portion 101 further includes a cable substrate 108 for connecting the signal wires 109 with the sensor signal substrate 104 and the sensor ground substrate 105.

Each of the signal wires 109 includes a signal line 109a for transmitting an electric signal from the main body of the ultrasonic diagnostic apparatus (not shown), which performs various ultrasonic signal processing, to the sensor portion or transmitting an electric signal converted from an ultrasonic wave including information on the living body to the main body of the ultrasonic diagnostic apparatus, and a ground line 109b for supplying the ground potential to the ultrasonic element 103 in the sensor portion. Preferably, the signal wires 109 have a coaxial structure in which central copper wires are surrounded by an inner shielding member such as a metal braided wire. The plurality of signal wires 109 are bundled and protected by the sheath 111. The sheath 111 can be made of an insulating material such as vinyl chloride, silicon, and the like, for example. Preferably, the cable shield 110 made of, for example, a metal braided wire, a metal foil, or the like is provided between the signal wires 109 and the sheath 111 for the shielding against extraneous electromagnetic waves and the radiation of electromagnetic waves.

The signal wires 109 are connected with the cable substrate 108. As the cable substrate 108, an insulating substrate with a conductive layer formed on its surface can be used as in the case of the sensor signal substrate 104. Further, the cable substrate 108 may be mounted with an electronic circuit. The conductive layer of the cable substrate 108 is patterned into a predetermined shape, which forms a signal pattern and a ground pattern. The signal pattern and the ground pattern of the cable substrate 108 are connected electrically with the signal line and the ground line of the signal wires, respectively.

The signal pattern of the cable substrate 108 further is connected electrically with the conductive layer of the sensor signal substrate 104. The connection between the cable substrate 108 and the sensor signal substrate 104 can be made, for example, by wire bonding, thermocompression bonding, or via a connector such as a card edge connector or the like.

The ground pattern of the cable substrate 108 further is connected electrically with the conductive layer 105b of the sensor ground substrate 105. In the present embodiment, the connection between the ground pattern of the cable substrate 108 and the conductive layer 105b of the sensor ground substrate 105 is made via a relay ground substrate 112. As the relay ground substrate 112, a conductive substrate such as a metal substrate made of, for example, a copper wire, a copper foil film, or the like can be used. The dimensions of the relay ground substrate 112 are not particularly limited. However, in order to reduce the ground resistance further, the relay ground substrate 112 preferably has a large cross sectional area and a short distance between the ground pattern of the cable substrate 108 and the conductive layer 105b of the sensor ground substrate 105. In the case where a plurality of the cable substrates 108 are provided, the relay ground substrate 112 connected with each of the cable substrates 108 is connected with the sensor ground substrate 105.

The relay ground substrate 112 is connected with the conductive layer 105b of the sensor ground substrate 105. For this connection, preferably, a drawn end portion (portion to be connected with the relay ground substrate 112) of the sensor ground substrate 105 is bent, particularly at an angle of 90° or more, and further preferably at an angle of about 180°. This allows the conductive layer 105b of the sensor ground substrate 105 to be exposed outside, thereby facilitating the connection between the conductive layer 105b and the relay ground substrate 112. In order to reduce the ground resistance, preferably, a connection area between the relay ground substrate 112 and the conductive layer 105b of the sensor ground substrate 105 is as large as possible.

Further, the relay ground substrate 112 is connected with the ground pattern of the cable substrate 108. Preferably, this connection is made such that the relay ground substrate 112 covers a connecting portion between the sensor signal substrate 104 and the cable substrate 108 as shown in FIG. 1. This arrangement allows the relay ground substrate 112 to function as a shielding plate for shielding the connecting portion between the sensor signal substrate 104 and the cable substrate 108, thereby increasing durability to withstand electromagnetic waves. As a result, there is no need to provide a shielding plate, and therefore it becomes possible to manufacture the ultrasonic probe easily and downsize the housing. In order to reduce the ground resistance, preferably, a connection area between the relay ground substrate 112 and the ground pattern of the cable substrate 108 is as large as possible.

The connector portion 102 includes a connector 115 for connecting with the main body and pins 116, each being connected with the signal line 109a or the ground line 109b. These components are accommodated in a connector housing 113. The connector housing 113 can be made of, for example, metal, resin, or the like, and is provided with a conductive layer 114 made of metal or the like on its inner wall surface. The cable shield 110 is connected with a metal portion on an outer periphery of the connector for connecting with the main body, the metal portion being insulated from the pins, or with the conductive layer 114 on the inner surface of the connector housing 113, and is to be connected with a frame ground or a signal ground of the main body of the ultrasonic diagnostic apparatus when the ultrasonic probe is connected with the main body of the ultrasonic diagnostic apparatus.

Next, a description will be given of the effects achieved by the ultrasonic probe thus configured.

In the above-described ultrasonic probe, the conductive layer 105b of the sensor ground substrate 105 and the ground pattern of the cable substrate 108 are connected via the relay ground substrate 112 as described above. Therefore, unlike the case where the conductive layer 105b and the ground pattern are connected via a connector, it is possible to avoid an increase in resistance due to limitations on the number of connector poles, resulting in a reduction in ground resistance between the sensor ground substrate 105 and the cable substrate 108. Consequently, the reduction in ground resistance suppresses a change in ground potential due to a noise current induced by extraneous electromagnetic waves. As a result, an adverse effect on a reception signal due to the change in ground potential is reduced, and image noise can be prevented from being caused, resulting in an ultrasonic image with high quality.

The connection between the cable portion 101 and the sensor portion 100 is made at at least two points, i.e., the connecting portion between the cable substrate 108 and the sensor signal substrate 104 and a connecting portion between the cable substrate 108 and the sensor ground substrate 105. Therefore, the connection strength between the cable portion 101 and the sensor portion 100 is increased. In particular, the use of the relay ground substrate 112 achieves the following effect. That is, even when a tensile stress is applied between the cable substrate 108 and the sensor signal substrate 104, the tension of the relay ground substrate 112 prevents a break in the ultrasonic probe due to the sensor signal substrate 104 and the cable substrate 108 becoming detached from each other, or the like.

Second Embodiment

The first embodiment has been described by taking as an example the case where the conductive layer of the sensor ground substrate and the ground pattern of the cable substrate are connected via the relay ground substrate. However, in the present embodiment, the conductive layer and the ground pattern may be connected directly with no relay ground substrate provided therebetween. Such an embodiment will be described below.

Figure 2:
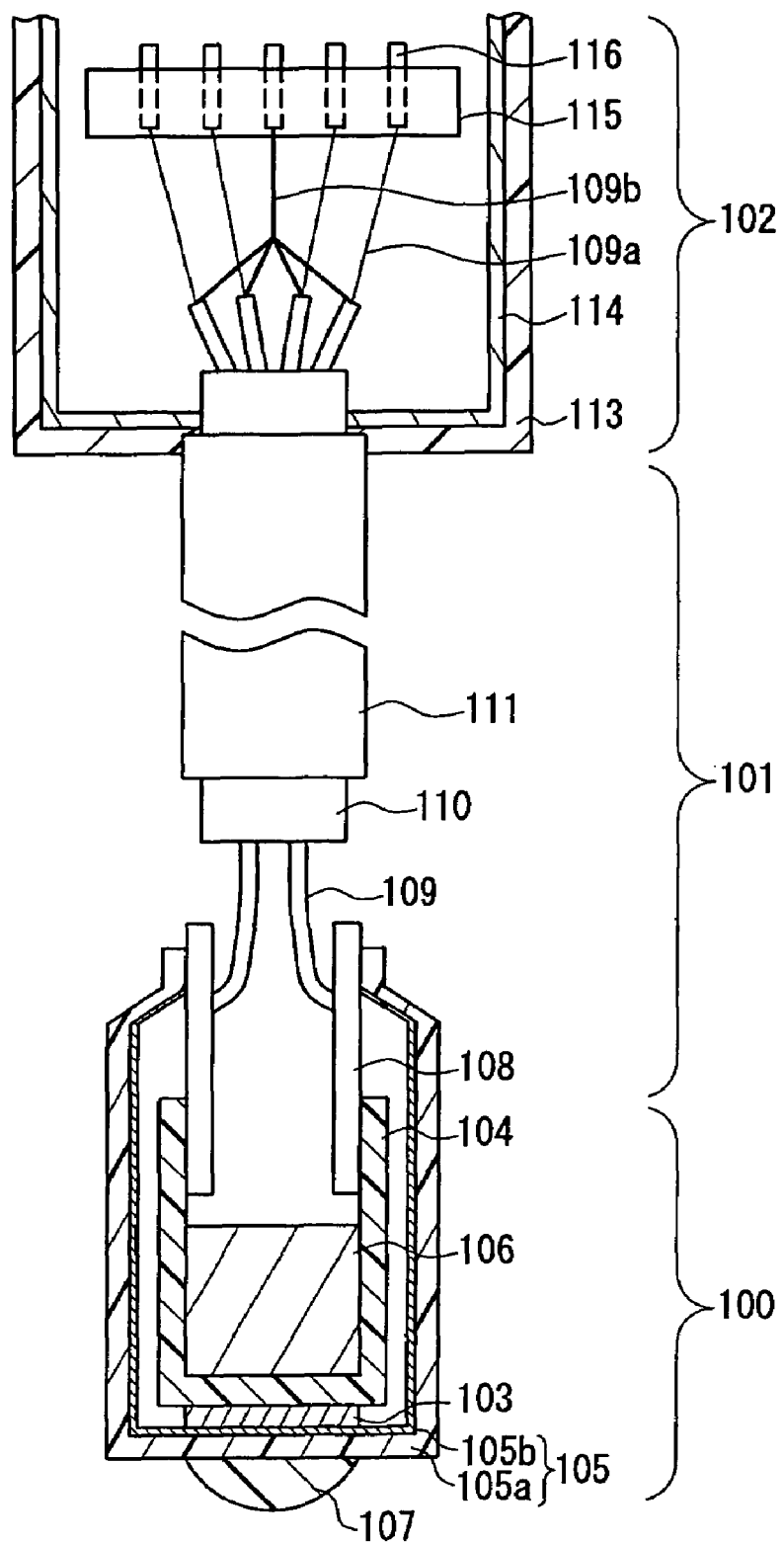
FIG. 2 is a cross-sectional view showing an example of an ultrasonic probe according to a second embodiment of the present invention.

FIG. 2 is a schematic cross-sectional view showing an example of an ultrasonic probe according to a second embodiment of the present invention. This ultrasonic probe includes a sensor portion 100, a cable portion 101, and a connector portion 102 as in the first embodiment.

The sensor portion 100 includes an ultrasonic element 103 and a sensor signal substrate 104 and a sensor ground substrate 105 connected with the ultrasonic element 103. In the example shown in FIG. 2, the sensor signal substrate 104 is arranged so as to cover an entire back surface of the ultrasonic element 103, and is drawn from both side surface sides of the ultrasonic element 103. The sensor ground substrate 105 is arranged so as to cover an entire ultrasonic wave transmitting/receiving surface of the ultrasonic element 103, and is drawn from both the side surface sides of the ultrasonic element 103. Thus, the sensor ground substrate 105 can be arranged so as to cover the ultrasonic wave transmitting/receiving surface and both side surfaces of the ultrasonic element 103. This arrangement allows a conductive layer 105b of the sensor ground substrate 105 to function as a shielding plate for shielding the ultrasonic element 103, thereby increasing durability to withstand electromagnetic waves.

The material, the structure, and the like of each of the components of the sensor potion 100 are substantially the same as those in the first embodiment. In particular, in the example shown in the present embodiment, the sensor ground substrate 105 is drawn from both the side surfaces of the ultrasonic element 103 so as to cover the entire ultrasonic wave transmitting/receiving surface reliably. Thus, a significant effect can be achieved when a material having an acoustic matching function is used for the sensor ground substrate 105.

The cable portion 101 includes a plurality of signal wires 109, each including a signal line 109a and a ground line 109b, a sheath 111, and cable substrates 108, each including a signal pattern and a ground pattern, as in the first embodiment. In the example shown in FIG. 2, the two cable substrates 108 are used, each being connected with drawn portions of the sensor signal substrate 104 and the sensor ground substrate 105, respectively, drawn on both the side surface sides of the ultrasonic element 103.

The signal pattern of the cable substrate 108 is connected electrically with the signal line 109a of the signal wire and the sensor signal substrate 104 in the sensor portion. These connections are made in the same manner as in the first embodiment.

The ground pattern of the cable substrate 108 is connected electrically with the ground line 109b of the signal wire and the sensor ground substrate 105. In the present embodiment, the ground pattern of the cable substrate 108 and the conductive layer 105b of the sensor ground substrate 105 are connected directly via solder, for example. Preferably, as shown in FIG. 2, the cable substrate 108 and the sensor ground substrate 105 are connected so that the sensor ground substrate 105 covers at least a part of a connecting portion between the sensor signal substrate 104 and the cable substrate 108. This arrangement allows the sensor ground substrate 105 to function as a shielding plate for shielding the connecting portion between the sensor signal substrate 104 and the cable substrate 108, thereby increasing durability to withstand electromagnetic waves. In order to reduce the ground resistance further, preferably, a connection area between the sensor ground substrate 105 and the ground pattern of the cable substrate 108 is as large as possible.

The material, the structure, and the like of each of the components of the cable potion 101 are substantially the same as those in the first embodiment.

Also, the structure of the connector portion 102 is substantially the same as that in the first embodiment, and a description thereof will be omitted.

The above description has been given taking as an example the case where the sensor signal substrate and the sensor ground substrate are drawn from both the side surface sides of the ultrasonic element. However, as in the first embodiment, these substrates may be drawn only from one side surface side of the ultrasonic element.

However, preferably, these substrates are drawn from both the side surface sides of the ultrasonic element, since, as described above, such a structure allows the sensor ground substrate to cover both the side surfaces of the ultrasonic element, thereby increasing durability to withstand electromagnetic waves. In addition, when the substrates are drawn from both the side surface sides, the sensor ground substrate 105 can cover the connecting portion between the cable substrate 108 and the sensor signal substrate 104 entirely as shown in FIG. 2 so as to shield this connecting portion, thereby increasing durability to withstand electromagnetic waves. As a result, there is no need to provide a shielding plate, and therefore it becomes possible to manufacture the ultrasonic probe easily and downsize the housing.

In the above-described ultrasonic probe, the sensor ground substrate 105 and the cable substrate 108 are connected directly. Therefore, as in the first embodiment, unlike the case where these substrates are connected via a connector, it is possible to avoid an increase in resistance due to limitations on the number of connector poles, resulting in a reduction in ground resistance between the sensor ground substrate and the cable substrate. Consequently, it is possible to suppress a change in ground potential due to a noise current induced by extraneous electromagnetic waves, resulting in an ultrasonic image with high quality.

In particular, in the present embodiment, since the sensor ground substrate 105 and the cable substrate 108 are connected directly, fewer connecting points via solder or the like are required than in the first embodiment using the relay ground substrate. As a result, it is possible to provide good workability for the manufacture and to suppress thermal damage to the cable portion and the sensor portion due to solder or the like.

Further, the connection between the cable portion and the sensor portion is made at at least two points, i.e., the connecting portion between the cable substrate and the sensor signal substrate and a connecting portion between the cable substrate and the sensor ground substrate. Therefore, the connection strength between the cable portion and the sensor portion is increased.

Third Embodiment

As described in the first and second embodiments, a sensor ground substrate can function as a shield.

In order to increase the operability by reducing the size and weight of an ultrasonic probe, a housing for accommodating a sensor portion is required to be downsized. However, when a shielding plate is provided additionally, the housing needs to be provided with enough space therein in view of the shape and thickness of the shielding plate, which makes it difficult to realize a reduction in size and weight. Further, when a cable connector portion is surrounded by a shielding plate, it is impossible to load the portion with a sufficient sealing material, and a structure therein may not be fixed sufficiently. Further, it is impossible to cover an ultrasonic wave transmitting/receiving surface of an ultrasonic element with a shielding plate, and thus it is difficult to prevent the intrusion of electromagnetic waves into the ultrasonic element.

However, as described above, according to one embodiment of the present invention, the sensor ground substrate can function as a shield, which eliminates the need to provide a shielding plate additionally. Accordingly, the above-mentioned problems also can be solved.

In the present embodiment, a description will be given of a configuration that allows the shielding effect of the sensor ground substrate to be increased particularly.

Figure 3:
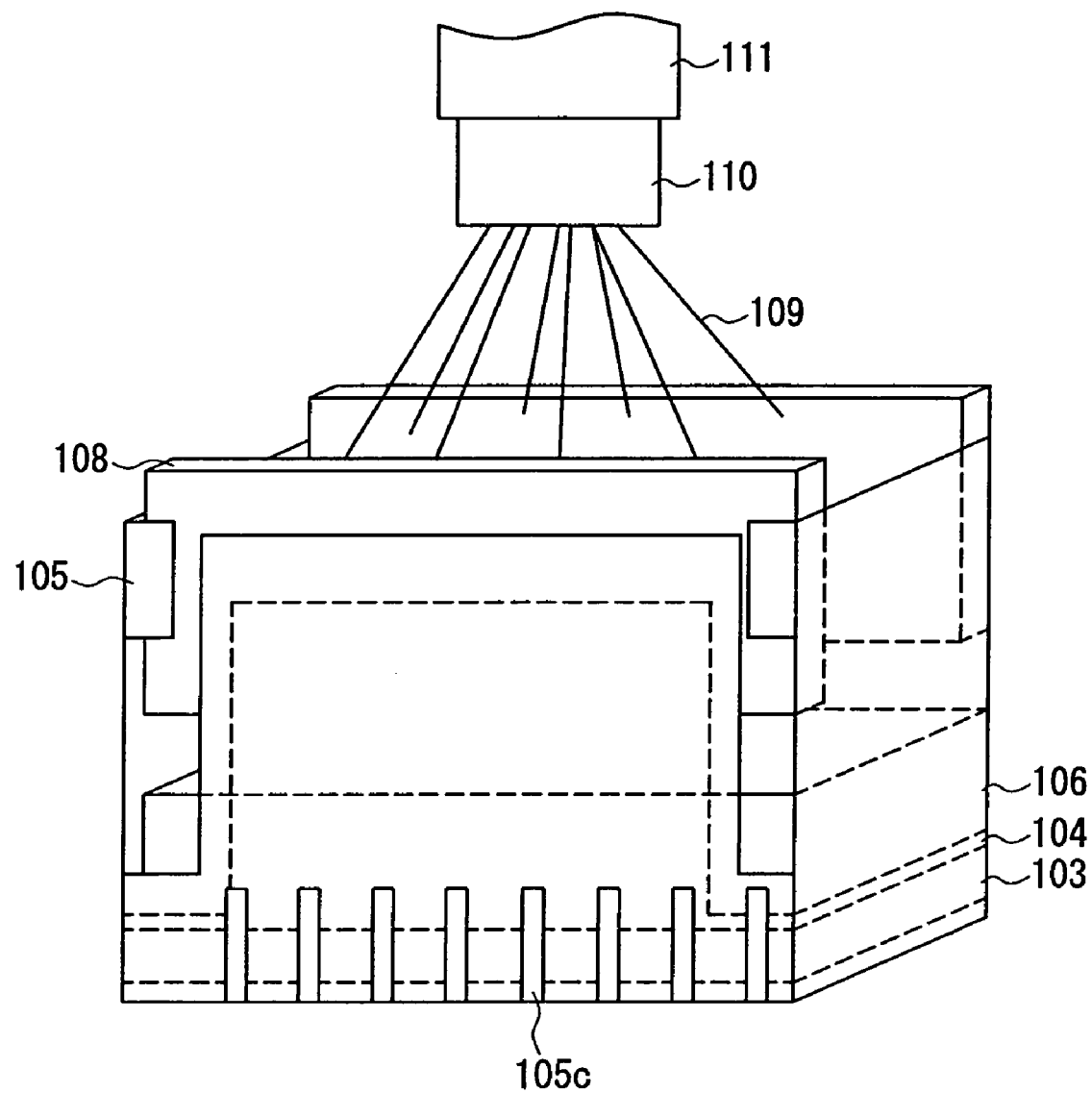
FIG. 3 is a cross-sectional view showing an example of an ultrasonic probe according to a third embodiment of the present invention.

FIG. 3 is a schematic perspective view showing an example of an ultrasonic probe according to a third embodiment of the present invention. This ultrasonic probe has substantially the same structure as in the second embodiment except for the shape of a sensor ground substrate 105. Thus, a detailed description will be given of the shape of the sensor ground substrate 105.

As in the second embodiment, a sensor portion includes an ultrasonic element 103 and a sensor signal substrate 104 and the sensor ground substrate 105 connected with the ultrasonic element 103. The sensor signal substrate 104 is arranged so as to cover an entire back surface of the ultrasonic element 103, and is drawn from both side surface sides of the ultrasonic element 103.

The sensor ground substrate 105 is arranged so as to cover an entire ultrasonic wave transmitting/receiving surface of the ultrasonic element 103, and is drawn from both the side surface sides of the ultrasonic element 103 as in the case of the sensor signal substrate 104. Further, as shown in FIG. 3, the sensor ground substrate 105 also covers side surfaces of the ultrasonic element 103 other than the side surfaces over which the sensor signal substrate 104 is drawn, that is, side surfaces adjacent to the side surfaces over which the sensor signal substrate 104 is drawn. This configuration allows the shielding effect of the sensor ground substrate 105 on the ultrasonic element 103 to be increased further.

As in the second embodiment, a cable portion includes a plurality of signal wires 109, each including a signal line and a ground line, a sheath 111, and cable substrates 108, each including a signal pattern and a ground pattern. As shown in FIG. 3, the two cable substrates 108 are used, each being connected with drawn portions of the sensor signal substrate 104 and the sensor ground substrate 105, respectively, drawn on both the side surface sides.

The ground pattern of the cable substrate 108 is connected electrically with the ground line of the signal wire 109 and the sensor ground substrate 105. As shown in FIG. 3, the cable substrate 108 and the sensor ground substrate 105 are connected so that the sensor ground substrate 105 covers a connecting portion between the sensor signal substrate 104 and the cable substrate 108 entirely. Further, as shown in FIG. 3, the sensor ground substrate 105 covers not only surfaces of the cable substrate 108 on which the ground pattern is formed but also surfaces perpendicular thereto (i.e., side surfaces). This configuration allows the shielding effect of the sensor ground substrate 105 on the cable substrate 108 to be increased further.

Figure 4:
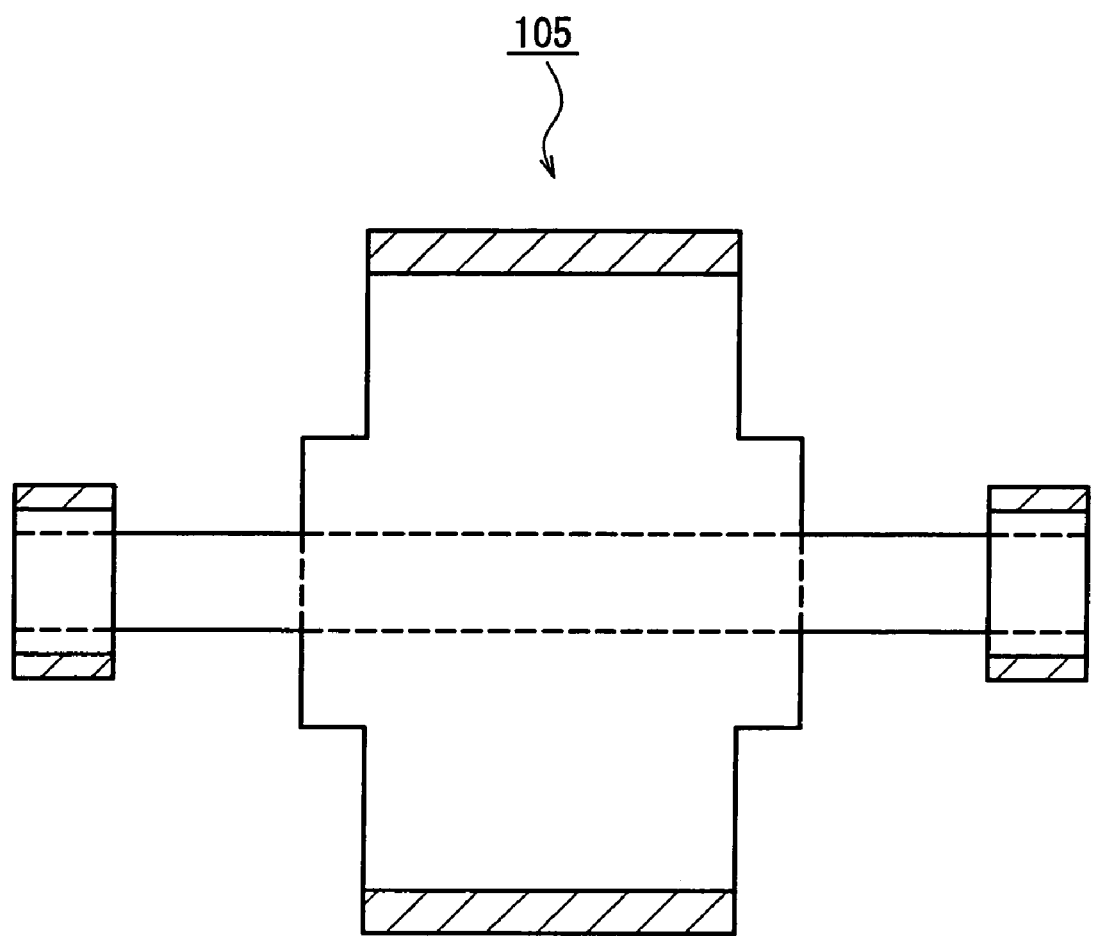
FIG. 4 is a development of a sensor ground substrate of the ultrasonic probe according to the third embodiment.
Figure 5:
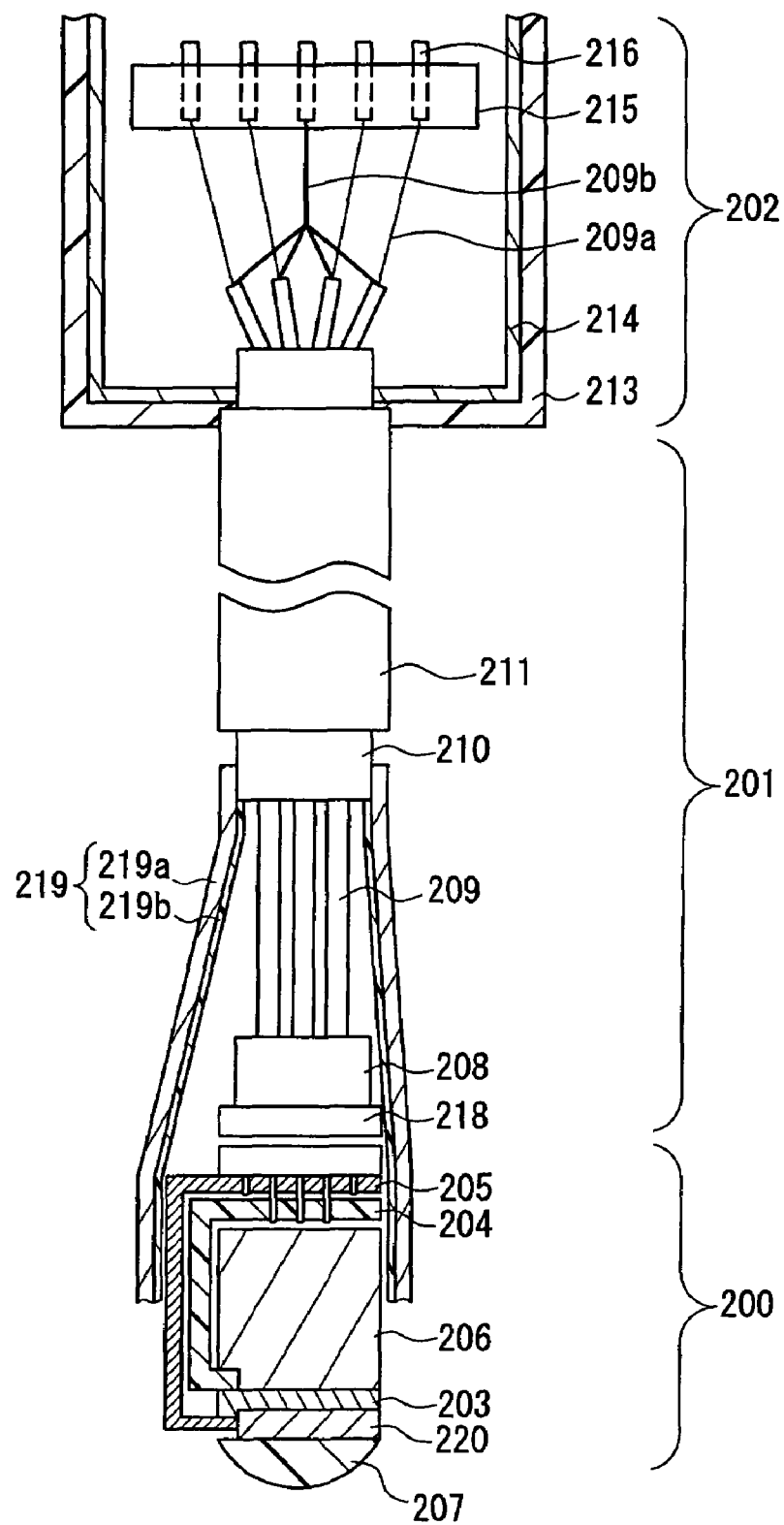
FIG. 5 is a cross-sectional view showing a conventional ultrasonic probe.

FIG. 4 is a development of the sensor ground substrate 105. As shown in FIG. 4, the sensor ground substrate 105 is composed of a bottom surface portion, which is a surface that covers the ultrasonic wave transmitting/receiving surface of the ultrasonic element, and side surface portions, all four sides of the bottom surface portion being connected to the side surface portions. In FIG. 4, shaded areas indicate connecting portions with the cable substrate.

Preferably, a plurality of grooves 105c are formed in the bottom surface portion of the sensor ground substrate. These grooves are formed so as to divide the ultrasonic element electrically into a plurality of oscillators. The grooves weaken mechanical binding between adjacent oscillators or increase independence of mechanical oscillation of the oscillators, thereby improving crosstalk and widening an angle of beam spread. Generally, the grooves are filled with an insulating material such as epoxy resin, silicon, and the like, and a softer filling material increases the independence of the oscillators more.

The sensor ground substrate 105 is arranged so as to surround a periphery (all four sides) of the ultrasonic element 103, the sensor signal substrate 104, and the cable substrate 108 with the side surface portions thereof. At this time, preferably, the side surface portions of the sensor ground substrate 105 that are drawn over the side surfaces (side surfaces of the cable substrate 108) of the ultrasonic element 103 other than the side surfaces over which the sensor signal substrate 104 is drawn are connected with the cable substrate 108 or the other side surface portions of the sensor ground substrate 105 via solder or the like. This connection allows the sensor ground substrate 105 to retain its shape.

As described above, in the present embodiment, the sensor ground substrate 105 is arranged so as to surround the periphery of the ultrasonic element 103, the sensor signal substrate 104, and the cable substrate 108. Therefore, the shielding effect of the sensor ground substrate 105 on the ultrasonic element 103, the sensor signal substrate 104, the cable substrate 108, and the connecting portion therebetween is increased. Therefore, it is possible to increase durability to withstand electromagnetic waves, and to reduce a noise current due to the intrusion of electromagnetic waves or the like. As a result, there is no need to provide a shielding plate additionally, and therefore it becomes possible to manufacture the ultrasonic probe easily and downsize the housing.

INDUSTRIAL APPLICABILITY

The ultrasonic probe according to the present invention allows ground resistance between the sensor ground substrate and the cable substrate to be reduced, so that a change in ground potential due to a noise current induced by extraneous electromagnetic waves is suppressed. As a result, an adverse effect on a reception signal due to the change in ground potential is reduced, and noise can be prevented from being caused on an ultrasonic diagnostic image. Therefore, this ultrasonic probe can be applied effectively to ultrasonic diagnostic apparatuses to be utilized in various medical fields.

The invention claimed is:

1. An ultrasonic probe, comprising: a piezoelectric element for transmitting and receiving an ultrasonic signal; a signal line for transmitting an electric signal to or from the piezoelectric element; and a ground line for supplying a ground potential to the piezoelectric element, the ultrasonic probe further comprising:
   a sensor signal substrate and a sensor ground substrate connected electrically with the piezoelectric element; and
   a cable substrate that electrically connects the sensor signal substrate and the sensor ground substrate with the signal line and the ground line, respectively,
   wherein the sensor ground substrate and the cable substrate are connected directly or via a relay ground substrate as a conductive substrate, and
   at least a part of the cable substrate is covered with the sensor ground substrate or the relay ground substrate.

2. The ultrasonic probe according to claim 1, wherein at least a part of the sensor signal substrate is covered with the sensor ground substrate or the relay ground substrate.

3. The ultrasonic probe according to claim 1, wherein a connecting portion between the sensor signal substrate and the cable substrate is covered with the sensor ground substrate or the relay ground substrate.

4. The ultrasonic probe according to claim 3, wherein the connecting portion between the sensor signal substrate and the cable substrate is covered with the sensor ground substrate or the relay ground substrate entirely.

5. The ultrasonic probe according to claim 1, wherein at least a part of the piezoelectric element is covered with the sensor ground substrate or the relay ground substrate.

6. The ultrasonic probe according to claim 5, wherein an ultrasonic wave transmitting/receiving surface of the piezoelectric element is covered with the sensor ground substrate or the relay ground substrate.

7. The ultrasonic probe according to claim 6, wherein the ultrasonic wave transmitting/receiving surface and peripheral surfaces of the piezoelectric element are covered with the sensor ground substrate or the relay ground substrate.

8. ultrasonic probe according to claim 6, wherein a plurality of grooves are formed on a part of the sensor ground substrate or the relay ground substrate that covers the ultrasonic wave transmitting/receiving surface of the piezoelectric element, the grooves dividing the piezoelectric element electrically into a plurality of oscillators.

9. The ultrasonic probe according to claim 6,
   wherein the sensor ground substrate is arranged so as to surround a periphery of the piezoelectric element, the sensor signal substrate, and the cable substrate, and
   a portion of the sensor ground substrate that is drawn over a surface of the piezoelectric element other than a surface connected with the sensor signal substrate is connected with the cable substrate or a part of the sensor ground substrate.

* * * * *